United States Patent
Milanese

(10) Patent No.: US 9,605,016 B2
(45) Date of Patent: Mar. 28, 2017

(54) METHOD OF ESTERIFICATION OF CARBOXYL GROUPS PRESENT ON MULTIHYDROXYL CYCLIC POLYENE MOLECULAR STRUCTURES CARRYING BASIC NITROGEN GROUPS

(71) Applicant: Alberto Milanese, Monza (IT)

(72) Inventor: Alberto Milanese, Monza (IT)

(*) Notice: Subject to any disclaimer, the term of this patent is extended or adjusted under 35 U.S.C. 154(b) by 23 days.

(21) Appl. No.: 14/816,114

(22) Filed: Aug. 3, 2015

(65) Prior Publication Data

US 2017/0037074 A1    Feb. 9, 2017

(51) Int. Cl.
*C07H 17/08*    (2006.01)

(52) U.S. Cl.
CPC .................................. *C07H 17/08* (2013.01)

(58) Field of Classification Search
None
See application file for complete search history.

(56) References Cited

U.S. PATENT DOCUMENTS 3,961,047 A    6/1976    Bruzzese et al.
4,365,058 A    12/1982    Falkowski et al.

*Primary Examiner* — Layla Berry
(74) *Attorney, Agent, or Firm* — Silvia Salvadori, P.C.; Silvia Salvadori

(57) ABSTRACT

Disclosed is a process for the preparation of partricin alkyl esters which involves reacting partricin in a solvent with primary alkyl alcohols in the quantity of 5 to 1000 moles per mole of partricin in the presence of carbodiimides, and optionally in the presence of acylation catalysts and/or nitrogen bases or anhydrous acids.

8 Claims, No Drawings

METHOD OF ESTERIFICATION OF CARBOXYL GROUPS PRESENT ON MULTIHYDROXYL CYCLIC POLYENE MOLECULAR STRUCTURES CARRYING BASIC NITROGEN GROUPS

The present invention relates to a process for the preparation of carboalkoxy derivatives of cyclic polyenes of natural origin carrying other functional groups (hydroxyl and nitrogen) that potentially interfere with the desired esterification reaction; the process according to the invention, which involves nucleophilic substitution on an activated acyl group instead of the alkylation procedure used to date, takes place rapidly and unequivocally, without any interference.

PRIOR ART

Typical multifunctionalised cyclic polyene structures of natural origin are those of the macrolide antibiotics, such as erythromycin, josamycin and rosaramicin. They include partricin of formula (I) and its methyl ester mepartricin (II). The latter is widely used in the treatment of benign prostate hypertrophy (U.S. Pat. No. 4,237,117). Partricin, produced from *Streptomyces* strains (U.S. Pat. No. 3,773,925 and GB 1462442), exists in two variants, partricin A and partricin B, depending on whether a methyl substituent is present instead of a hydrogen atom in the —NH2 aniline group present in the molecule. Mepartricin, which exists in form A and form B, obviously also presents said difference. The ratio between form A and B in partricin depends on the fermentation conditions. In mepartricin, however, it depends not only on the starting partricin, but also on the final purification conditions, as there is a small difference in solubility between the two forms. Said ratio has a well-defined limit in pharmaceutical grade mepartricin.

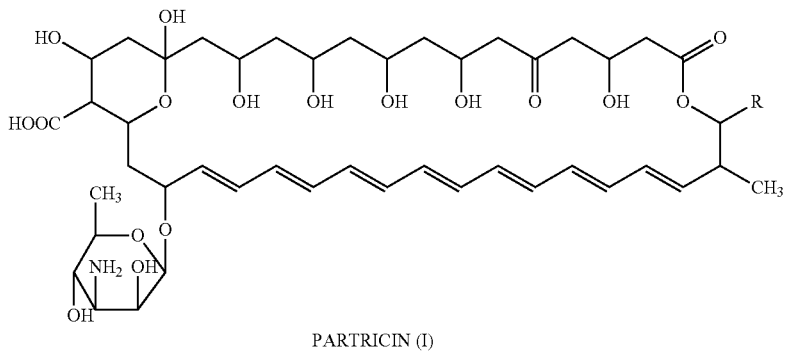

PARTRICIN (I)

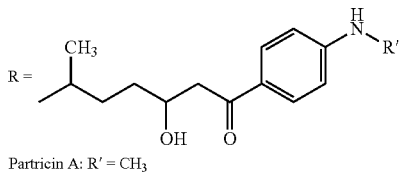

Partricin A: R' = CH₃
Partricin B: R' = H

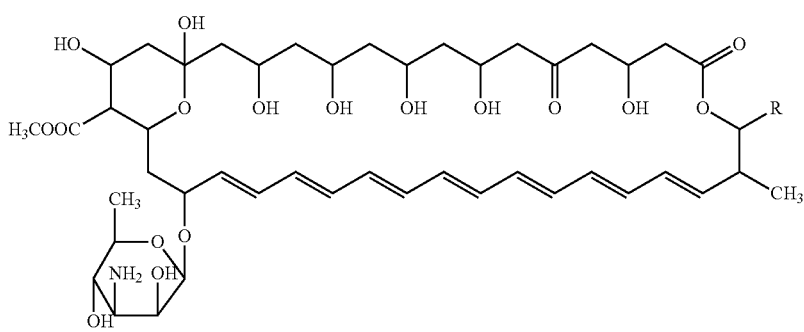

MEPARTRICIN (II)

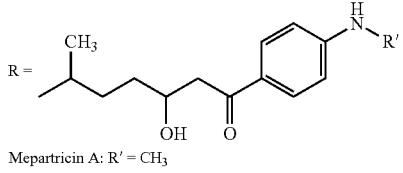

Mepartricin A: R' = CH₃
Mepartricin B: R' = H

Only mepartricin, a semisynthetic derivative obtained by methylation on the carboxyl group of partricin, is used as a medicament.

Said methylation (T. Bruzzese et al., Experientia 28, 1515 (1972), and DE 2154436) has always constituted a considerable problem, both at the actual synthesis step and at the purification step. The first problem is the low solubility of both products in most common solvents; another problem is the delicacy of this type of molecular structure, which is highly sensitive to light, heat and pH values distant from neutrality, whether acid or basic. The molecule also tends to polymerise, and esterification with methanol and acid catalysts is impossible, for example: either the reaction does not proceed or the molecule degrades. The use of alkylating agents such as methyl or ethyl iodide or dimethyl or diethyl sulphate in a neutral or moderately alkaline environment leads to irreversible alkylation of the two amino groups present; protecting them does not solve the problem, because the deprotection conditions damage the molecule. The presence of multiple hydroxyl groups can create competition in esterification, as well as paving the way for dehydration reactions and tautomeric rearrangements, and the presence of a hemiacetal group is liable to cause competitive opening and methylation. Finally, the presence of a lactone structure involves sensitivity to alkalis, while the polyene structure is subject to addition or cleavage of bonds due to the reduction in the overall bond energy.

The only reagent to date which has provided a satisfactory compromise between these difficulties and the need to obtain mepartricin of the necessary quality under mild conditions, in reasonable times and with acceptable yields and costs, is diazomethane.

However, the use of said reagent is not problem-free; although the procedure is performed under well-controlled conditions, there is always a partial insertion into the N—H bonds, giving rise to impurities carrying one or two methyls on the nitrogen groups. Combination reactions on the C═C double ethylene bonds giving cyclopropanes are also possible. To limit the formation of these and other impurities, the methylation reaction is stopped when the conversion is between 70 and 80%. The unmethylated partricin must then be separated, and is difficult to recover.

Basically, the standard yield of mepartricin of a quality corresponding to the specific requirements for the medicament is around 20% by weight of the partricin used.

Another problem is that diazomethane, a highly toxic, carcinogenic and explosive gas, is known to be hazardous. Its use requires particular structures and permits held by very few companies, which perform this reaction as contractors, involving very high additional costs.

A procedure for preparing partricin esters other than the methyl ester is reported in U.S. Pat. No. 3,961,047; once again, however, the higher homologues of diazomethane (diazoethane, diazopropane and diazobutane) are used.

The hazardous nature of these reagents is similar to that of diazomethane, and the products obtained require laborious purification procedures, including elution on chromatography columns.

U.S. Pat. No. 4,365,058 discloses the use of dicyclohexylcarbodiimide as carboxyl group esterification promoter for the macrolides nystatin, aureofacin, candicidin, pimaricin, amphotericin B, polyfungin and the N-derivatives thereof. However, the esterification products obtained after many hours of reaction still require purification involving a step on a chromatography column to achieve a sufficient degree of purity; in view of its poor solubility the inevitable by-product of the reaction, dicyclohexylurea, is difficult to separate from complex products which are also poorly soluble, such as macrolides. Finally, an attempted application of said method to partricin failed due to its low solubility in conditions compatible with the stability of partricin and the low yield of the product, which was highly contaminated by impurities and reaction by-products, leading to the need for very complex, expensive purification procedures.

DESCRIPTION OF THE INVENTION

It has now been found that under suitable reaction conditions some other carbodiimides normally used in polypeptide synthesis allow rapid, highly efficient, clean substitution of the carboxyl hydroxyl of partricin by methanol or other alcohols, thus obtaining the corresponding ester with excellent yields and high purity, even in the case of the merely precipitated crude product.

The carbodiimides used can be the symmetrical or asymmetrical type, and are selected from N,N'-diisopropylcarbodiimide, N-(3-dimethylaminopropyl)-N'-ethylcarbodiimide hydrochloride, N-(3-dimethylaminopropyl)-N'-ethylcarbodiimide base, and N-(3-dimethylaminopropyl)-N'-ethylcarbodiimide methyl iodide.

The preferred carbodiimides are N,N'-diisopropylcarbodiimide and N-(3-dimethylaminopropyl)-N'-ethylcarbodiimide hydrochloride; the latter is also available on the market as a base or methyl iodide, which are equally reactive, although the hydrochloride is the most available and manageable form. The former presents the advantages that it has a reasonable price, is in the liquid state at room temperature, and that it and the resulting urea are completely soluble in the most common solvents. The later, together with the corresponding urea is also reactive and soluble in water. The aggressiveness and toxicity of both are far lower than those of diazomethane and other diazoalkanes. With moderate molar excesses (from 1.2 to 5 moles per mole of partricin), the esterification reaction is completed in 7 or 8 hours with the former and less than an hour with the latter.

The reaction proceeds according to the following SCHEME, which is common to all the carbodiimides:

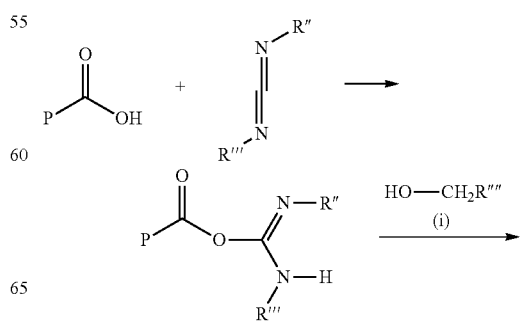

-continued

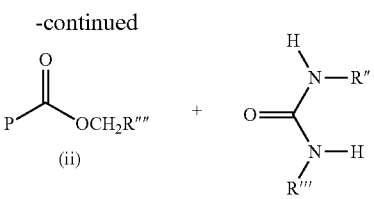

P—COOH = Partricin

P—COOH$_2$R'''' = Partricin Esters

R' = R''' = isopropyl: N, N'-diisopropylcarbodiimide
R'' = ethyl; R''' = 3-dimetylaminopropyl base, hydrochloride or methyl iodide; N-(3-dimethylaminopropyl)-N'etylcarbodiimide base, hydrochloride or methyl iodide
R'' and R''' are equarl or different alkyls, cycloalkyls, dialkylaminoalkyls as bases or salified with acids or quaternised with alkylating agents; other possible carbodiimides.
R'''' = H; (i) = methanol; (iii) = mepartricin
R'''' = straight or branched C1 to C4 alkyl; correspoinding partricin (i) alcohols and (ii) esters The process according to the invention therefore comprises reacting partricin in a solvent with primary alkyl alcohols in the quantity of 5 to 1000 moles per mole of partricin in the presence of carbodiimides, and optionally in the presence of acylation catalysts and/or nitrogen bases or anhydrous acids.

The alcohols are used in large excess, almost as co-solvents, to completely inhibit possible competition by the two amino groups and the other hydroxyls present in the molecule. Moreover, the amino groups are somewhat sterically impeded, and the non-carboxyl hydroxyls are all secondary, and therefore much less reactive than that of the primary alcohol used.

As stated, the process comprises the nucleophilic substitution on an acyl group activated by the adduct with carbodiimide, which is the only one present in the molecule. This prevents alkylation by an alkylating agent like diazomethane, which is powerful and not very selective, and reacts not only on the carboxyl hydroxyl, but also on the two amino groups and the ethylene double bonds, generating many impurities, at least four of which are known and accepted up to high percentages. The process therefore takes place unequivocally, without the formation of impurities. The only impurities present derive from the starting partricin.

The presence of an acylation catalyst accelerates the reaction; the pH needs to be maintained between 5 and 9 by adding calculated quantities of nitrogen bases such as triethylamine or N-ethyldiisopropylamine, or anhydrous mineral acids such as hydrochloric acid in non-aqueous solvents. Suitable solvents are those already indicated for partricin, such as anhydrous dimethylsulphoxide, pyridine, dimethylformamide and dimethylacetamide. They are used in quantities ranging from 5 to 15 times in volume of the weight of the partricin. As stated, the reaction is completed in 1 to 8 hours, depending on the carbodiimide used; with N-(3-dimethylaminopropyl)-N'-ethylcarbodiimide hydrochloride, using a moderate molar excess, 90% of the end product was produced in 5 minutes; the reaction is carried out at a temperature of 10° to 30° C. for the time required, without any exothermy or endothermy being observed; it is then stopped by adding water, maintaining the temperature below 20° C. so as to release the hydration heat of the solvents.

Following subsequent strong dilution with cold water the crude mepartricin, or the ester corresponding to the alcohol used, precipitates, and is collected on a filter or centrifuge. When this very simple isolation procedure is used, the yield is close to the theoretical yield, by weight. The assay value always exceeds 75%, and often 80%. The chromatographic purity of the crude product exceeds 85%, and often 90%.

Using the well-known purification and crystallisation methods, with no need for steps on chromatography columns or resins, a high-quality mepartricin is obtained that not only meets the strictest specifications but is superior to that of any batch produced with the current technology, free of all the known impurities, and has a weight yield exceeding 50% of the partricin used.

The partricin is dissolved, even only partly, in one of the solvents indicated (anhydrous dimethylsulphoxide, pyridine, dimethylformamide or dimethylacetamide), used in the ratio of 5 to 15 ml/g, at a temperature ranging from room temperature to 30° C. Methanol, or the other desired primary alcohol, is added in the ratio of 2 to 10 ml/g of partricin; a large volume of alcohol only, such as 50 ml/g or more, can be used as solvent. The solubilisation of partricin is aided by small additions of tertiary nitrogen bases, such as triethylamine or N-ethyldiisopropylamine, in quantities equimolar to the acid groups present in the reaction environment, or by small additions of anhydrous mineral acids, such as anhydrous hydrochloric acid in titrated solution, in quantities equimolar to the basic groups also present in the reaction. The carbodiimide is then added, in a molar ratio of 1.2 to 5 moles/mole of partricin, and the mixture is stirred at room temperature until the reaction is complete, i.e. when the residual partricin is less than 0.4%, monitoring the process with a TLC or HPLC assay. On completion of the reaction, usually 1 to 8 hours from $T_0$, depending on the conditions and the reagents, water is added, gradually and keeping the temperature under 20° C., in quantities such as to cause complete precipitation of the reaction product: usually 50 ml/g of partricin. The precipitate is stirred for 15-30 minutes, collected on a Büchner funnel, filter press or centrifuge, and washed thoroughly with water. As stated, the yield is almost quantitative, the purity exceeds 85%, and the assay value exceeds 75%. This crude product is then purified to pharmaceutical grade by known procedures.

Some examples of the use of the invention described above are set out below.

EXAMPLE 1

1.18 g of partricin, corresponding to about a millimole, is stirred in 12 ml of dimethylsulphoxide at room T; 5 ml of methanol is added. The mixture is stirred for about 15 min at room T, and N-(3-dimethylaminopropyl)-N'-ethylcarbodiimide hydrochloride (0.958 g, 5.0 mmols) is added. The resulting mixture is stirred at room T for 4 hours. Without exceeding 20° C., the mixture is diluted with water (50 ml) and stirred for a further 30 min. The precipitate formed is collected on a Büchner funnel, and washed thoroughly with water. After drying under vacuum at a T below 30° C., 1.13 g of crude mepartricin with an assay value of 75% and purity of 85% is obtained.

EXAMPLE 2

1.18 g of partricin is stirred in 12 ml of dimethylsulphoxide at room T; 4-dimethylaminopyridine (1.22 g, 10 mmols) and 5 ml of methanol are added. The mixture is stirred for about 15 min at room T, and N-(3-dimethylaminopropyl)-N'-ethylcarbodiimide hydrochloride (0.958 g=5.0 mmols) is added. The resulting mixture is stirred at room temperature for 3 hours. Without exceeding 20° C. the mixture is diluted with 50 ml of water and stirred for a further 30 min. The precipitate formed is collected on a Büchner funnel, and washed thoroughly with water. After drying under vacuum at a T below 30° C., 1.14 g of crude mepartricin with an assay value of 76% and purity of 86% is obtained.

EXAMPLE 3

1.18 g of partricin is stirred in 12 ml of dimethylsulphoxide at room T; 5 ml of methanol and triethylamine is added (0.612 g=0.838 ml=6.0 mmols). The mixture is stirred for about 15 min at room T, and N-(3-dimethylaminopropyl)-N'-ethylcarbodiimide hydrochloride (0.958 g, 5.0 mmols) is added. The resulting mixture is stirred at room temperature for 8 hours. Without exceeding 20° C., the mixture is diluted with 50 ml of water and stirred for a further 30 min. The precipitate formed is collected on a Büchner funnel, and washed thoroughly with water. After drying under vacuum at a T below 30° C., 1.11 g of crude mepartricin with an assay value of 78% and purity of 85% is obtained.

EXAMPLE 4

1.18 g of partricin is stirred in 15 ml of pyridine at room T; 4-dimethylaminopyridine (0.122 g, 1 mmols) and 5 ml of methanol are added. The mixture is stirred for about 15 min at room T, and N-(3-dimethylaminopropyl)-N'-ethylcarbodiimide hydrochloride (0.958 g, 5.0 mmols) is added. The resulting mixture is stirred at room temperature for 4 hours. Without exceeding 20° C. the mixture is diluted with 50 ml of water and stirred for a further 30 min. The precipitate formed is collected on a Büchner funnel, and washed thoroughly with water. After drying under vacuum at a T below 30° C., 1.10 g of crude mepartricin with an assay value of 75% and purity of 85% is obtained.

EXAMPLE 5

1.18 g of partricin is stirred in 15 ml of pyridine at room T; 4-dimethylaminopyridine (0.610 g, 5 mmols) and 5 ml of methanol are added. The mixture is stirred for about 15 min at room T, and N,N'-diisopropylcarbodiimide (0.631 g=0.774 ml=5.0 mmols) is added. The resulting mixture is stirred at room temperature for 5 hours. Without exceeding 20° C., the mixture is diluted with 50 ml of water and stirred for a further 30 min. The pH is adjusted to >9 with triethylamine, and the precipitate formed is collected on a Büchner funnel and washed thoroughly with water. After drying under vacuum at a T below 30° C., 1.09 g of crude mepartricin with an assay value of 78% and purity of 88% is obtained.

EXAMPLE 6

1.18 g of partricin is stirred in 15 ml of pyridine at room T; 4-dimethylaminopyridine (0.122 g, 1 mmols) and 5 ml of methanol are added. The mixture is stirred for about 15 min at room T, and a solution of 4M HCl in 1 ml of dioxane and N,N'-diisopropylcarbodiimide (0.631 g=0.774 ml=5.0 mmols) is added. The resulting mixture is stirred at room temperature for 8 hours. Without exceeding 20° C. the mixture is diluted with 50 ml of water and stirred for a further 30 min. The pH is adjusted to >9 with triethylamine, and the precipitate formed is collected on a Büchner funnel and washed thoroughly with water. After drying under vacuum at a T below 30° C., 0.98 g of crude mepartricin with an assay value of 75% and purity of 89% is obtained.

EXAMPLE 7

1.18 g of partricin is suspended in 50 ml of methanol at room T; 4-dimethylaminopyridine (0.122 g=1 mmol) is added. The mixture is stirred for about 15 min at room T, and a solution of 4M HCl in 1 ml of dioxane and N-(3-dimethylaminopropyl)-N'-ethylcarbodiimide hydrochloride (0.958=5.0 mmols) is added. The resulting mixture is stirred at room temperature for 2 hours. Without exceeding 20° C. the methanol is evaporated under vacuum, and the resulting mixture is diluted with 50 ml of water and stirred for a further 30 min. The pH is adjusted to >9 with triethylamine, and the precipitate formed is collected on a Büchner funnel and washed thoroughly with water. After drying under vacuum at a T below 30° C., 1.11 g of crude mepartricin with an assay value of 82% and purity of 93% is obtained.

EXAMPLE 8

1.18 g of partricin is stirred in 15 ml of pyridine at room T; 4-dimethylaminopyridine (0.122 g=1 mmol) and 5 ml of methanol are added. The mixture is stirred for about 15 min at room T, and triethylamine (0.252 g=2.5 mmol) and N-(3-dimethylaminopropyl)-N'-ethylcarbodiimide hydrochloride (0.480 g=2.5 mmols) are added. The resulting mixture is stirred at room temperature for 4 hours. Without exceeding 20° C. the mixture is diluted with 50 ml of water and stirred for a further 30 min. The pH is adjusted to >9 with triethylamine, and the precipitate formed is collected on a Büchner funnel and washed thoroughly with water. After drying under vacuum at a T below 30° C., 1.01 g of crude mepartricin with an assay value of 78% and purity of 91% is obtained.

EXAMPLE 9

1.18 g of partricin is stirred in 15 ml of pyridine at room T; 4-dimethylaminopyridine (0.122 g=1 mmol) and 5 ml of methanol are added. The mixture is stirred for about 15 min at room T, and N-(3-dimethylaminopropyl)-N'-ethylcarbodiimide hydrochloride (0.240 g=1.25 mmols) is added. The resulting mixture is stirred at room temperature for 8 hours. Without exceeding 20° C. the mixture is diluted with 50 ml of water and stirred for a further 30 min. The pH is adjusted to >9 with triethylamine, and the precipitate formed is collected on a Büchner funnel and washed thoroughly with water. After drying under vacuum at a T below 30° C., 1.01 g of crude mepartricin with an assay value of 77% and purity of 87% is obtained.

EXAMPLE 10

1.18 g of partricin is stirred in 15 ml of N,N-dimethylacetamide at room T; 4-dimethylaminopyridine (0.122 g=1 mmol) and 5 ml of methanol are added. The mixture is stirred for about 15 min at room T, and N-(3-dimethylaminopropyl)-N'-ethylcarbodiimide hydrochloride (0.958 g=5.0 mmols) is added. The resulting mixture is stirred at room temperature for 4 hours. Without exceeding 20° C., the mixture is diluted with 50 ml of water and stirred for a further 30 min. The pH is adjusted to >9 with triethylamine, and the precipitate formed is collected on a Büchner funnel and washed thoroughly with water. After drying under vacuum at a T below 30° C., 1.12 g of crude mepartricin with an assay value of 75% and purity of 85% is obtained.

EXAMPLE 11

1.18 g of partricin is stirred in 15 ml of pyridine at room T; 4-dimethylaminopyridine (0.122 g=1 mmol) and 5 ml of ethanol are added. The mixture is stirred for about 15 min at room T, and N-(3-dimethylaminopropyl)-N'-ethylcarbodiimide hydrochloride (0.958 g=5.0 mmols) is added. The resulting mixture is stirred at room temperature for 4 hours. Without exceeding 20° C. the mixture is diluted with 50 ml of water and stirred for a further 30 min. The pH is adjusted to >9 with triethylamine, and the precipitate formed is collected on a Büchner funnel and washed thoroughly with water. After drying under vacuum at a T below 30° C., 1.08 g of crude partricin ethyl ester with a purity of 85% is obtained.

EXAMPLE 12

As for example 10, replacing the ethanol with 5 ml of n-propanol. 1.18 g of partricin n-propyl ester with a purity of 86% is obtained.

EXAMPLE 13

As for example 11, replacing the n-propanol with 5 ml of n-butanol. 1.16 g of partricin n-butyl ester with a purity of 85% is obtained.

The invention claimed is:

1. A process for the preparation of partricin alkyl esters, which comprises reacting partricin with primary alkyl alcohols in amounts of 5 to 1000 moles per mole of partricin in a solvent, in the presence of carbodiimides selected from N,N'-diisopropylcarbodiimide, N-(3-dimethylaminopropyl)-N'-ethylcarbodiimide hydrochloride, N-(3-dimethylaminopropyl)-N'-ethylcarbodiimide base and N-(3-dimethylaminopropyl)-N'-ethylcarbodiimide methyl iodide, and optionally in the presence of acylation catalysts and/or nitrogen bases or anhydrous acids.

2. The process according to claim 1, wherein the carbodiimide is N-(3-dimethylaminopropyl)-N'-ethylcarbodiimide hydrochloride.

3. The process according to claim 1, wherein the carbodiimides are used in a molar excess of 1.2 to 5 moles per mole of partricin.

4. The process according to claim 1, wherein the alcohol is methanol.

5. A process according to claim 1, wherein the solvents are dimethylsulphoxide, pyridine, N,N-dimethylformamide, N,N-dimethylacetamide or the same alcohol as used as reagent.

6. A process according to claim 1, wherein the acylation catalyst is 4-dimethylaminopyridine.

7. A process according to claim 1, wherein the reaction is carried out in the presence of a titrated solution of anhydrous HCl in an anhydrous solvent.

8. A process according to claim 1, wherein the reaction is carried out until a residual content of unreacted partricin lower than 0.4% is obtained, and wherein the reaction product is recovered by dilution of the solvent with water, subsequent separation of the resulting precipitate, and washing thereof.

* * * * *